(12) United States Patent
Froimson (10) Patent No.: US 8,956,065 B2
(45) Date of Patent: Feb. 17, 2015

(54) APPLICATOR FOR DISPENSING A SURGICAL PREP SOLUTION

(75) Inventor: Mark I. Froimson, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 294 days.

(21) Appl. No.: 13/571,504

(22) Filed: Aug. 10, 2012

(65) Prior Publication Data

US 2013/0202482 A1 Aug. 8, 2013

Related U.S. Application Data

(60) Provisional application No. 61/521,925, filed on Aug. 10, 2011.

(51) Int. Cl.
*A61L 2/16* (2006.01)
*A61M 35/00* (2006.01)
*A61F 13/40* (2006.01)
*A61L 2/00* (2006.01)
*A61B 19/00* (2006.01)

(52) U.S. Cl.
CPC ............ *A61M 35/006* (2013.01); *A61L 2/0088* (2013.01); *A61L 2/16* (2013.01); *A61B 19/36* (2013.01)

USPC ............................ 401/194; 401/205; 401/263

(58) Field of Classification Search
CPC .... A61B 19/36; A61M 35/00; A61M 35/003; A61M 35/006; A61L 2/00; A61L 2/0005; A61L 2/0082; A61L 2/0088; A61L 2/16; A61L 2/18
USPC .................................. 401/194, 204, 205, 263
See application file for complete search history.

(56) References Cited

U.S. PATENT DOCUMENTS

| | | | | |
|---|---|---|---|---|
| 4,861,180 | A * | 8/1989 | Adams | 401/195 |
| 8,066,444 | B2 * | 11/2011 | Rippl et al. | 401/194 |
| 2001/0053305 | A1 * | 12/2001 | Berke et al. | 401/6 |
| 2006/0072962 | A1 | 4/2006 | Cybulski et al. | |
| 2010/0221193 | A1 | 9/2010 | Huang et al. | |

* cited by examiner

*Primary Examiner* — David Walczak
*Assistant Examiner* — Joshua Wiljanen
(74) *Attorney, Agent, or Firm* — Tarolli, Sundheim, Covell & Tummino LLP (57) ABSTRACT

An applicator for delivering a surgical prep solution onto a bodily surface includes a hollow member having a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer.

18 Claims, 5 Drawing Sheets

APPLICATOR FOR DISPENSING A SURGICAL PREP SOLUTION

RELATED APPLICATION

This application claims the benefit of U.S. Provisional Patent Application Ser. No. 61/521,925, filed Aug. 10, 2011, the entirety of which is hereby incorporated by reference.

TECHNICAL FIELD

The present invention relates to an applicator for dispensing a surgical prep solution, and more particularly to an applicator with an integrated timer for reducing the risk of fire associated with the use of surgical prep solutions.

BACKGROUND OF THE INVENTION

Pre-operative preparation of the skin with a topical antimicrobial agent is necessary to reduce the likelihood that the patient will contract a hospital-acquired infection during a surgery or surgical procedure. Typically, healthcare practitioners (e.g., prep nurses) apply a topical antimicrobial agent to a surgical or needle entry site before the procedure. Similarly, it is essential that medical devices that breach the skin be disinfected prior to penetrating the skin at an entry site or accessing an intravenous system. Healthcare practitioners typically disinfect these medical devices by applying an antimicrobial solution, e.g., alcohol, prior to use. Such treatment reduces the infection rate at the site or within the blood stream by hindering the growth of microorganisms or disinfecting a wound, surgical incision, or needle puncture site.

Healthcare practitioners have long used ethanol or isopropanol (either alone or as a solvent) along with other antimicrobial agents to disinfect the skin at the surgical incision or needle puncture site to reduce the population of bacteria, fungi, and some viruses at the site. Alcohol also provides rapid and sustained antimicrobial activity when it is combined with antimicrobial agents. However, alcohol-based surgical prep solutions are flammable, and certain surgical procedures cannot begin until the alcohol is completely evaporated. Hospital fires have been caused by unevaporated flammable solvents within surgical prep solutions. To help ensure patient safety, it is critical that healthcare practitioners be able to determine and document whether the flammable solvents within surgical prep solutions are completely evaporated prior to initiating energized surgical procedures, such as electrocautery.

SUMMARY OF THE INVENTION

According to one aspect of the present invention, an applicator for delivering a surgical prep solution onto a bodily surface comprises a hollow member having a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer.

According to another aspect of the present invention, a method is provided for applying a surgical prep solution onto a bodily surface. One step of the method includes providing an applicator comprising a hollow member having a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer. Next, the surgical prep solution is dispensed onto the bodily surface while at least one signal is generated by the timer. The medical procedure is then commenced once the at least one signal is no longer perceptible.

According to another aspect of the present invention, a method is provided for applying a surgical prep solution onto a bodily surface. One step of the method includes providing an applicator comprising a hollow member having a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer. Next, the surgical prep solution is dispensed onto the bodily surface. A medical procedure is commenced when the timer generates at least one signal.

A method for applying a surgical prep solution to a bodily surface is provided. One step of the method includes providing an applicator comprising a hollow member including a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer. The surgical prep solution is dispensed onto the bodily surface while the timer generates a first signal. Next, application of the surgical prep solution is discontinued when the timer generates a second signal. A medical procedure is then commenced once the combination of signals that has indicated separately the commencing, completion, and sufficient elapsing of time following prep application have so indicated.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Unless otherwise defined, all technical terms used herein have the same meaning as commonly understood by one of ordinary skill in the art to which the present invention pertains.

In the context of the present invention, the term "bodily surface" can refer to any surface of the human body (e.g., the skin) upon or about which a medical procedure can be performed.

As used herein, the term "medical procedure" can refer to surgical or invasive procedures that involve an entry or contact with a patient or subject, or that potentially compromises the integrity of the skin or other tissues. Non-limiting examples of surgical procedures can include: cardiothoracic surgery, vascular surgery, colon surgery, hip or knee arthroplasty, biliary surgery, vaginal or abdominal hysterectomy, percutaneous gastronomy, repair of long bone fractures, dental surgery, oral surgery, ear, nose or throat surgery, Cesarean section, etc. Non-limiting examples of invasive medical procedures can include: non-surgical dental procedures (e.g., tooth repairs and cleanings), bladder catheter insertions, insertion of nasal cannulas, biopsies, dermatological procedures, hair transplants, removal of a foreign object from the skin, eye, nasal, ear, or other body cavities, etc. It should be understood that the distinction between surgical procedures and invasive medical procedures can be somewhat arbitrary, and is meant to provide a general guideline for defining procedures where a patient or subject could be at risk of contracting an infection from the procedure.

As used herein, the term "electrical communication" can refer to the exchange of electron between two entities, which may be either in direct electrical communication (e.g., without electrons passing through a third entity) or indirect electrical communication (e.g., first and second entities that are capable of exchanging electrons with each other only via a third entity).

As used herein, the term "surgical prep solution" can refer to any antiseptic liquid (or combination of liquids) capable of disinfecting a bodily surface (e.g., a surgical field) prior to, during, or after a medical procedure. Examples of suitable surgical prep solutions can include those described in U.S. Pat. No. 4,584,192 and U.S. Pat. No. 4,542,012, the disclosures of which are incorporated herein by reference. In one example of the present invention, surgical prep solutions can include iodophoric skin tinctures, such as DURAPREP SURGICAL SOLUTION (3M, St. Paul, Minn.) or alcohol-based solutions, such as chlorhexidine-based solutions (e.g., CHLORAPREP (CareFusion, Leawood, Kans.)). Surgical prep solutions can additionally or optionally include (as the antimicrobial agent) iodine, an iodine complex, chlorhexidine, chlorhexidine salts, or combinations thereof. Iodine complexes may include iodophors, e.g., povidone-iodine USP. Chlorhexidine salts may include, e.g., chlorhexidine digluconate and chlorhexidine diacetate. Other antimicrobial agents may include C2-C5 lower alkyl alcohols (including, e.g., ethyl alcohol, 1-propanol, and 2-propanol), parachlorometaxylenol, triclosan, hexachlorophene, fatty acid monoesters of glycerin and propylene glycol, such as glycerol monolaurate, glycerol monocaprylate, glycerol monocaprate, propylene glycol monolaurate, propylene glycol monocaprylate, propylene glycol moncaprate, phenols, surfactants, and polymers that include a (C12-C22) hydrophobe and a quaternary ammonium group, polyquatenary amines, such as polyhexamethylene biguanide, quaternary ammonium silanes, silver, silver salts (such as silver chloride), silver oxide and silver sulfadiazine, methyl, ethyl, propyl and butyl parabens, octenidene, peroxides (e.g., hydrogen peroxide and benzoyl peroxide), and the like, as well as combinations thereof.

Figure 1A:
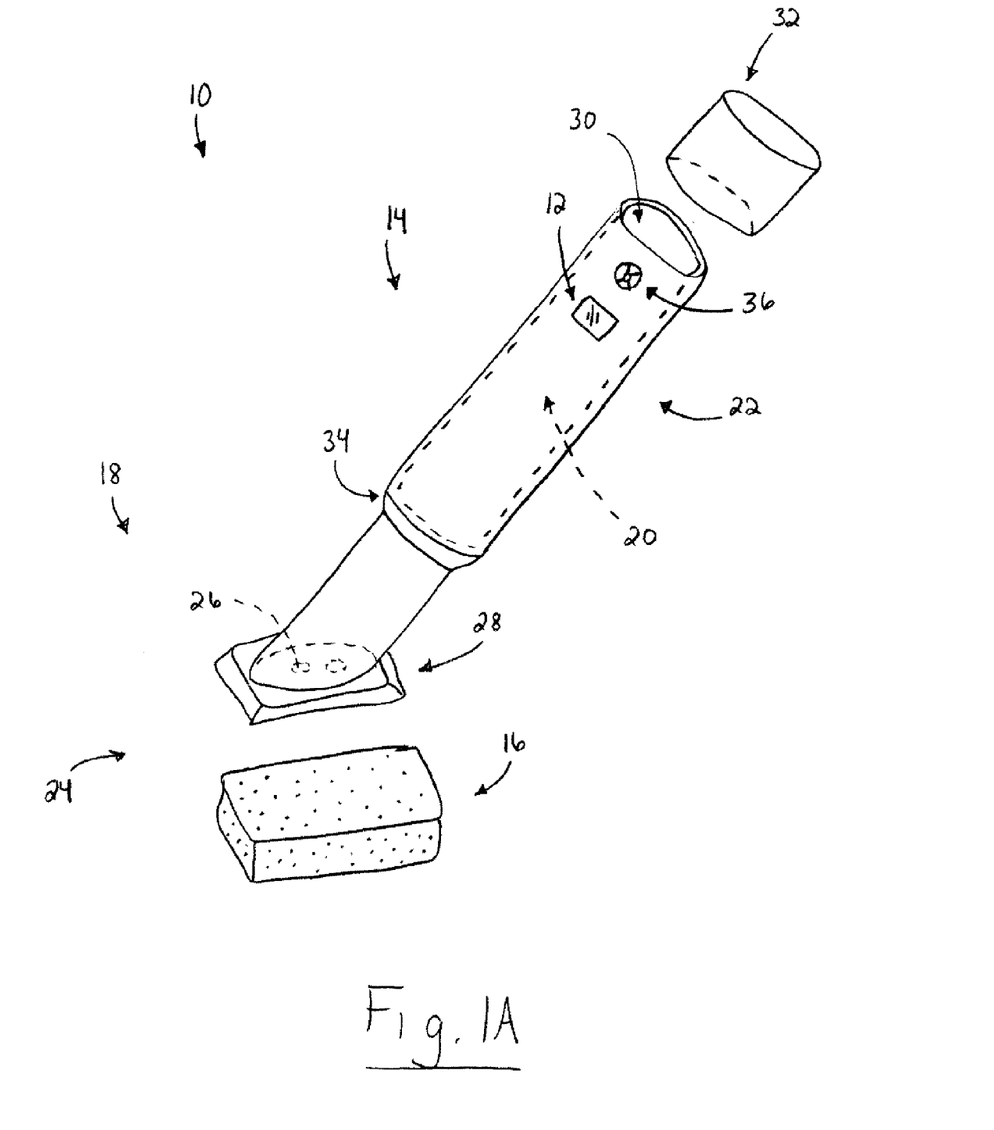
FIG. 1A is an exploded perspective view of an applicator for dispensing a surgical prep solution onto a bodily surface constructed in accordance with one aspect of the present invention.
Figure 1B:
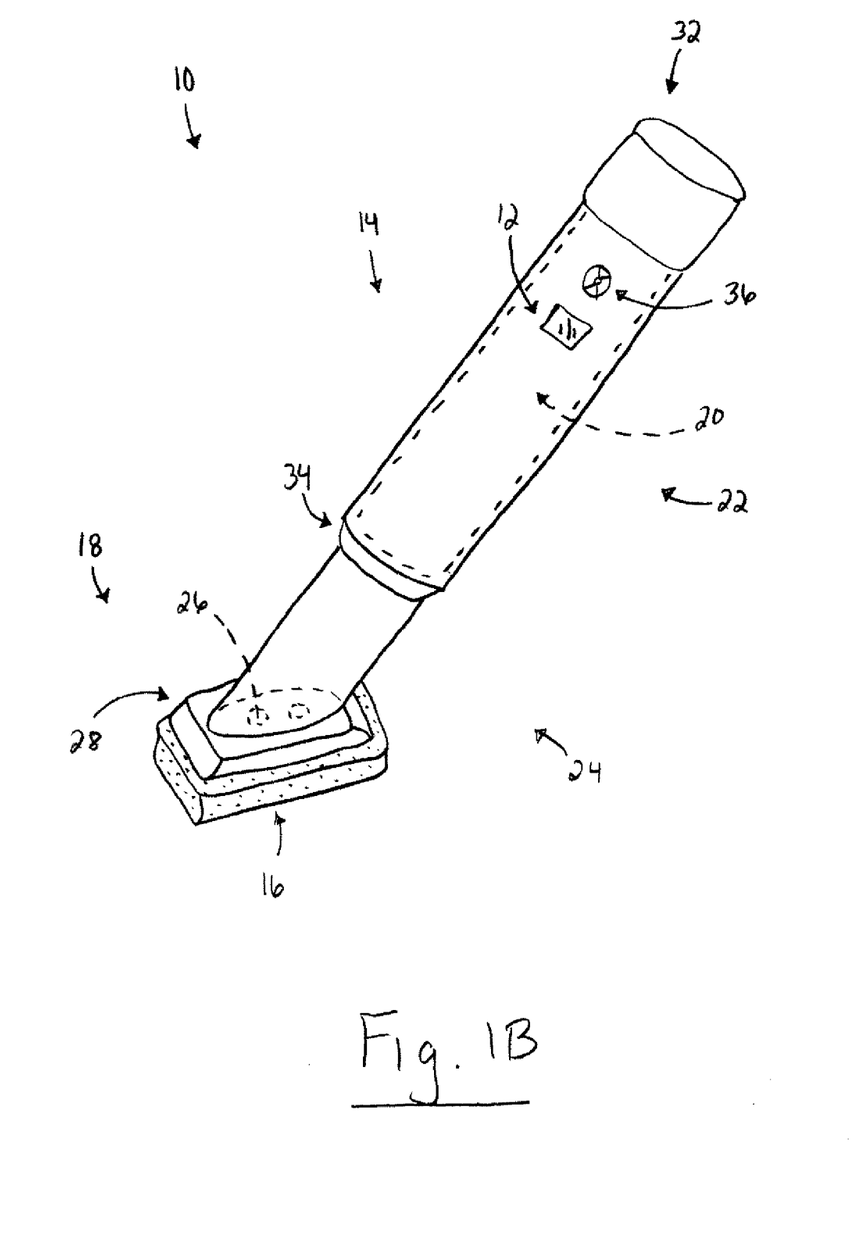
FIG. 1B is an assembled perspective view of the applicator in FIG. 1A.

The present invention relates to an applicator for dispensing a surgical prep solution, and more particularly to an applicator with an integrated timer for reducing the risk of fire associated with the use of surgical prep solutions. As representative of one aspect of the present invention, FIGS. 1A-B illustrate an applicator 10 for dispensing a surgical prep solution onto a bodily surface. Healthcare practitioners have long used surgical prep solutions, such as ethanol or isopropanol to disinfect the skin at a surgical incision or needle puncture site. Such alcohol-based surgical prep solutions, however, are flammable, and hospital fires have been caused by the unevaporated flammable solvents. Advantageously, the applicator 10 of the present invention includes a built-in timer 12 that automatically commences upon application of a surgical prep solution, thereby ensuring that a surgical team is aware that the applied prep solution has had sufficient time to dry or evaporate prior to commencement of a medical procedure. The present invention assists health care practitioners (e.g., a surgical team) in assessing the time that has lapsed following application of a surgical prep solution, consequently providing a safety check before initiating a medical procedure during which there may be a risk a of fire. Additionally, the present invention assists the health care team in providing a linkage to the electronic medical record to help document the compliance with appropriate prep application.

As shown in FIGS. 1A-B, one aspect of the present invention includes an applicator 10 comprising a hollow member 14, an absorbent pad 16 attached to a portion of the hollow member, a built-in timer 12, and a gating mechanism 18 (not shown in detail). In one example of the present invention illustrated in FIGS. 1A-B, the hollow member 14 can have an elongated configuration, which can serve as a handle. It will be appreciated, however, that the hollow member 14 can have any shape or configuration (e.g., square, rectangular, etc.) to facilitate ease of use by a healthcare practitioner. The hollow member 14 can be made of a molded plastic piece, such as a thermoplastic material compatible with the surgical prep solution to be dispensed.

The hollow member 14 includes a reservoir 20 adapted to hold a surgical prep solution. The reservoir 20 may be directly filled with a surgical prep solution or, alternatively, the reservoir may be adapted to support a container (not shown), such as a frangible ampoule containing a surgical prep solution. The container can form a barrier to materials and methods used in sterilization, such as ethylene oxide gas, irradiation methods, and hydrogen peroxide. Alternate embodiments to a frangible ampoule for delivering the surgical prep solution can include collapsible containers, such as those described in U.S. Pat. No. 6,422,778, or the pierceable container as described in Published Application No. 2004/0068218 A1, the entireties of which are hereby incorporated by reference. The container may, for example, be provided in a tube resembling a toothpaste tube. The container may be collapsible so that compression of the container causes the surgical prep solution to flow from the container into the absorbent pad 16.

Referring to FIGS. 1A-B, the hollow member 14 includes a tubular handle portion 22, a dispensing portion 24, a first orifice 26 with an integrally formed and radially-projecting flange 28 adapted to accept the absorbent pad 16, a second orifice 30 adapted to retain a cap 32, and a shoulder 34 disposed between the first and second orifices. For surgical prep applications, the hollow member 14 should be long enough to prevent contact of the patient by the person applying the surgical prep solution. The dispensing portion 24 can have a modular design so that the radially-projecting flange 28 and/or the absorbent pad 16 can be readily coupled (e.g., snapped-in) to the hollow member 14, thereby providing a reusable applicator 10.

The integrally-formed flange 28 surrounds the first orifice 26 and is angled from the longitudinal axis of the hollow member 14 by between about 30 and 90 degrees. In one example of the present invention, there is about a 45 degree angle between the flange 28 and the longitudinal axis of the hollow member 14.

The cap 32 covers the second orifice 30 of the hollow member 14. One example of a suitable configuration for the cap 32 is further described in U.S. Pat. No. 5,658,084, which is hereby incorporated by reference in its entirety. The cap 32 is adapted to transmit an actuation force to a container as the cap is axially displaced in the direction towards absorbent pad 16 to release the surgical prep solution from the container to the absorbent pad.

The absorbent pad 16 is attached to a portion of the hollow member 14. The absorbent pad 16 is in fluid communication with the reservoir 20 via the first orifice 26, of which there may be more than one. The absorbent pad 16 is attached to the flange 28 by a seal (not shown) formed between the absorbent pad and the flange. The seal between the absorbent pad 16 and the flange 28 may be formed by any suitable bonding technique(s) known in the art, such as adhesives, hot plate welding, solvent bonding, ultrasonic welding, inductive welding, and plastic rod welding. The absorbent pad 16 can be the equal to or larger than the size of the flange 28. For example, the absorbent pad 16 can be larger than the flange 28, which allows for soft edges and also facilitate prepping between digits of the human hand or other narrow prepping surfaces. While shown as a square, it will be appreciated that the absorbent pad 16 may be of any shape that makes fluid application convenient (e.g., rectangles, ellipses, circles, triangles, ovals, etc.).

The absorbent pad 16 can be selected from a variety of commercially available materials having a wide range of compression set ratios, densities and porosities. For a given volume, viscosity, density and surface tension of the liquid, wetting of the absorbent pad 16 can be accomplished by appropriate specification of the average pore size, pore size distribution, void volume fraction, and surface energy of the material from which the absorbent pad is formed. The compression state (i.e., compressed or uncompressed) and porosity of the absorbent pad 16 can be adjusted in relation to the viscosity, density, volume and surface tension of the surgical prep solution to be dispensed to allow a portion of the surgical prep solution contained in the applicator 10 to flow to the outer surface of the absorbent pad.

The absorbent pad 16 comprises a foam material compatible with the surgical prep solution to be dispensed. Examples of foam sponge materials include those prepared from thermoplastic materials, such as polyethylene and polyurethane. The foam material can be reticulated (open cell) or non-reticulated (closed cell) foam. The foam material can also be compressed (felted) or uncompressed. Many other materials for the absorbent pad 16 may be possible, including non-woven carded webs, filter material, knit pads, such as gauze, woven pads, and the like. These pads can be made from synthetic or natural polymers. It is also contemplated in the present invention that an additional layer of a fabric (not shown) can be placed over the absorbent pad 16, which may aid in coating uniformity.

The applicator 10 additionally includes a timer 12 that can automatically commence when a surgical prep solution is released. As described in more detail below, the timer 12 can indicate when a surgical prep solution has sufficiently dried or evaporated following application to a bodily surface. The timer 12 is operably connected to a portion of the hollow member 14. For example, the timer 12 can be built-in or integrally formed with the handle portion 22 of the hollow member 14. As described in more detail below, the timer 12 is capable of generating at least one signal upon activation (e.g., release of the surgical prep solution) or at a pre-determined period of time following activation. Release of the surgical prep solution from the reservoir 20 (or a container) into the absorbent pad 16 is prevented until the timer 12 is activated. It will be appreciated that activation of the timer 12 can be achieved not only by release of the surgical prep solution, but also via a control button (not shown) that can be manually actuated.

The timer 12 can include any type of clock (e.g., digital) capable of counting down from a specified time interval and/or counting upwards from zero (e.g., a stopwatch). When the specified time interval expires (or has been reached in the case of a stopwatch-type timer), the timer 12 can generate at least one signal. The at least one signal can be an audible signal (e.g., an alarm), a visible signal (e.g., a blinking LED light), or a combination thereof. As described below, any one or combination of the same or different audible or visible signals can be used to assist healthcare practitioners in determining and documenting whether flammable solvents used as part of surgical prep solutions are completely evaporated or dried prior to commencement of a medical procedure.

An audible signal may be transmitted through one or more acoustic elements (e.g., speakers) 36 that are in electrical communication with the timer 12. Such acoustic elements 36 may be operably integrated or built-into a portion of the hollow member 14. Alternatively, an audible signal may be transmitted through an acoustic element 36 that is an integral part of the timer 12 itself. As shown in FIGS. 1A-B, the timer 12 can include an optional display window, which is integrated into the hollow member 14 and capable of displaying the elapsed or total remaining time following activation of the timer. Additionally, the optional display window may be capable of displaying (e.g., continuous or intermittent flashing or blinking) one or combination of different colors as part of a visible signal.

The applicator 10 additionally includes a gating mechanism 18 for coordinating release of a surgical prep solution with activation of the timer 12. The gating mechanism 18 can be in electrical communication with the timer 12. As described in more detail below, the gating mechanism 18 and the timer 12 cooperatively function to enable passive and active mechanisms for releasing the surgical prep solution and causing the timer to generate at least one signal. The gating mechanism 18 can include one or a combination of elements (e.g., probes or electrodes) (not shown) that, when triggered, is/are capable of causing release of the surgical prep solution. The gating mechanism 18 can be triggered, for example, upon activation of the timer 12.

To coordinate release of the surgical prep solution with activation of the timer 12, the gating mechanism 18 and/or the timer can include circuitry (not shown) and/or software (not shown). Circuitry for use as part of the gating mechanism 18 and/or the timer 12 can include electrical circuitry having at least one discrete electrical circuit, electrical circuitry having at least one integrated circuit, electrical circuitry having at least one application-specific integrated circuit, or a microprocessor configured by a computer program that at least partially carries out processes described herein), electrical circuitry forming a memory device (e.g., forms of memory, such as random access, flash, read only, etc.), electrical circuitry forming a communications device (e.g., a modem, communications switch, optical-electrical equipment, etc.), and/or any non-electrical analog thereto, such as optical or other analogs. Those having skill in the art will recognize that the circuitry can be implemented in an analog fashion, a digital fashion, or some combination thereof.

Software that may be included as part of the gating mechanism 18 and/or the timer 12 can include one or more computer programs and related data that provide instructions to the circuitry. The software can comprise one or more known types of software, such as system software (e.g., an operating system), programming software (e.g., defining the syntax and semantics of various programs), and application software (e.g., end-user applications). Other examples of software can include firmware, device drivers, programming tools, and middleware.

It will be appreciated that the applicator 10 can additionally or optionally include hardware and software needed to provide a communication protocol (e.g., RF, Bluetooth, etc.) and thereby enable communication between the applicator and an electronic medical record (EMR) of a patient undergoing a medical procedure in which the applicator 10 is being used. By including a communication protocol as part of the applicator 10, the present invention not only provides an extra safety check during medical procedures, but improves EMR documentation by providing a "time stamp" to create medical proof of safety compliance.

Figure 2:
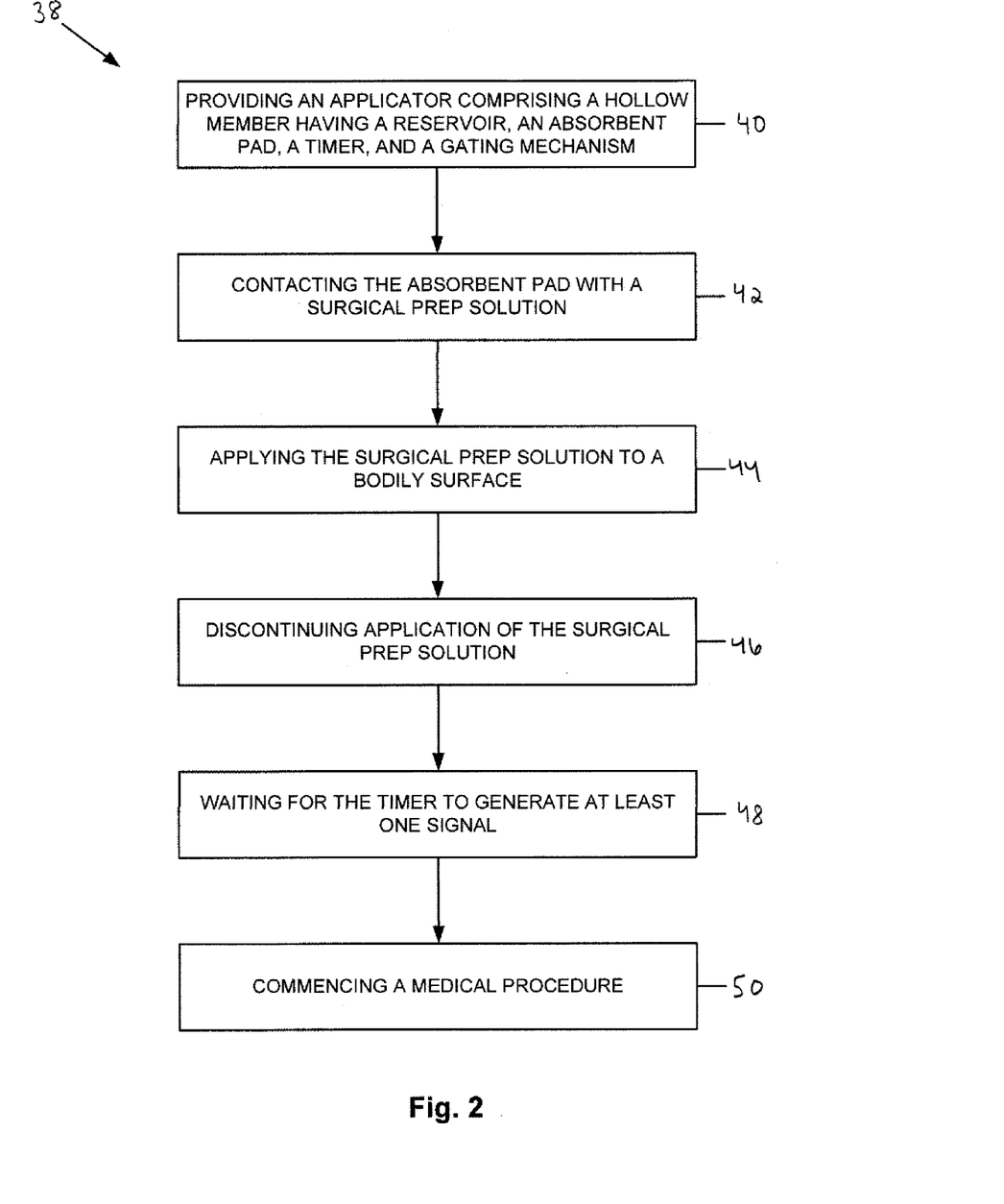
FIG. 2 is a process flow diagram illustrating a method for applying a surgical prep solution onto a bodily surface in accordance with another aspect of the present invention.

Another aspect of the present invention is illustrated in FIG. 2 and includes a method 38 for applying a surgical prep solution to a bodily surface using a passive mechanism. As shown in FIG. 2, the method 38 includes providing an applicator 10 at Step 40. The applicator 10 can be constructed in an identical or similar fashion as the applicator shown in FIGS. 1A-B. For example, the applicator 10 can comprise an elongated hollow member 14 having a reservoir 20, an absorbent pad 16 that is attached to a portion of the hollow member, a timer 12 that is operably connected to the hollow member, and a gating mechanism 18 in electrical communication with the timer. The reservoir 20 can be filled with a surgical prep solution (e.g., DURAPREP) or, alternatively, a container (e.g., a frangible ampoule) containing the surgical prep solution.

At Step 42, the surgical prep solution is released from the reservoir 20 (e.g., by compressing or breaking a container of the surgical prep solution) and contacts the absorbent pad 16. At or about the same time, the timer 12 is activated and, depending upon the preference of the user, the type of medical procedure, the type of surgical prep solution, etc., initiates a count-down or count-up sequence. The timer 12, however, does not generate at least one signal upon release of the surgical prep solution.

Once the absorbent pad 16 is saturated with the surgical prep solution, the surgical prep solution can be applied to a bodily surface (Step 44). The bodily surface onto which the surgical prep solution is applied will depend upon the type of medical procedure to be performed. For a Caesarian section, for example, the absorbent pad 16 can be contacted with the skin of a patient's abdomen. After appropriately applying the surgical prep solution to the bodily surface (e.g., the surgical site), use of the applicator 10 is discontinued by the user (Step 46).

After discontinuing use of the applicator 10, the user can wait for a period of time after which the timer 12 generates at least one signal (Step 48). For example, the timer 12 can generate an audible and/or visible signal for about 3-5 minutes following application of the surgical prep solution to the bodily surface. The period of time following application of the surgical prep solution (and before which at least one signal is generated) corresponds to the time needed for the surgical prep solution to evaporate or dry. Thus, once at least one signal is discerned by the healthcare practitioner(s), the healthcare practitioner(s) (e.g., surgical team) will know that the surgical prep solution is evaporated or dried.

At Step 50, the medical procedure can then be commenced without fear of igniting unevaporated surgical prep solution during the medical procedure.

Figure 3:
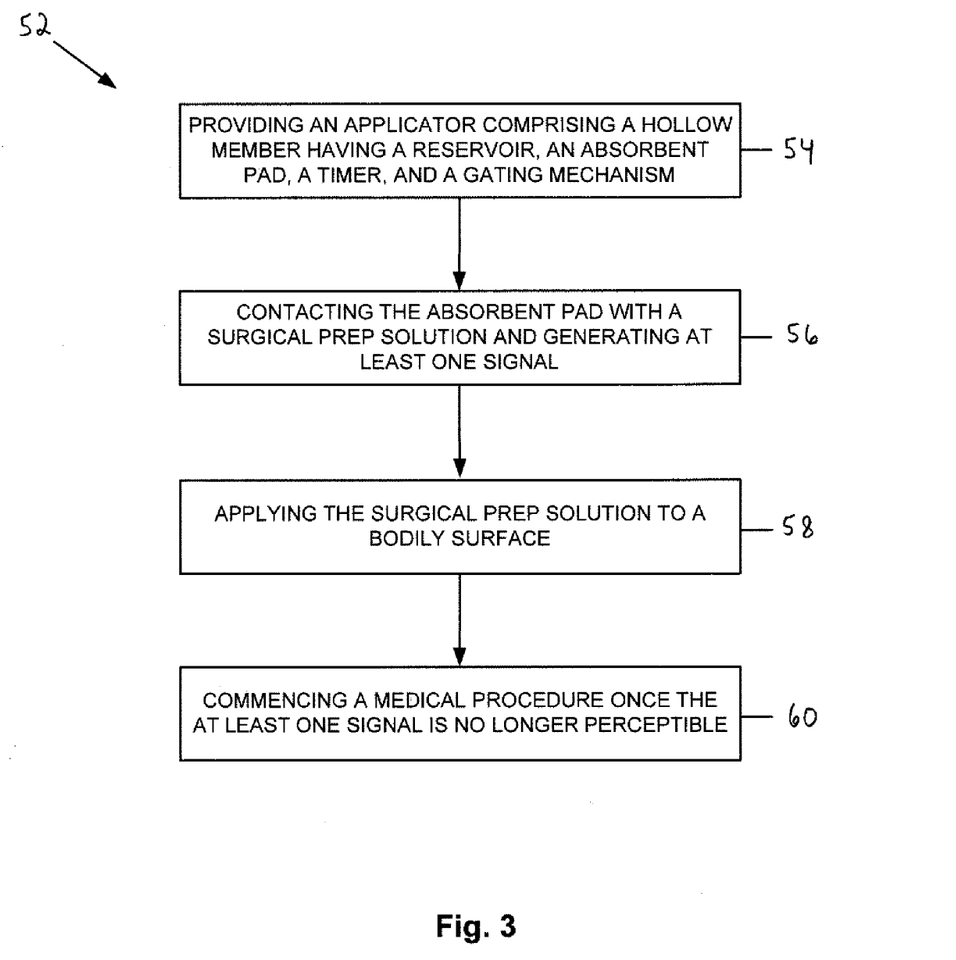
FIG. 3 is a process flow diagram illustrating a method for applying a surgical prep solution onto a bodily surface in accordance with yet another aspect of the present invention.

Another aspect of the present invention is illustrated in FIG. 3 and includes a method 52 for applying a surgical prep solution to a bodily surface using an active mechanism. As shown in FIG. 3, the method 52 includes providing an applicator 10 at Step 54. The applicator 10 can be constructed in an identical or similar fashion as the applicator shown in FIGS. 1A-B and described in the method 38 (FIG. 2) above.

At Step 56 (FIG. 3), the surgical prep solution is released from the reservoir 20 (e.g., by compressing or breaking a container of the surgical prep solution) and contacts the absorbent pad 16. At or about the same time, the timer 12 is activated and, depending upon the preference of the user, the type of medical procedure, the type of surgical prep solution, etc., initiates a count-down or count-up sequence. Activation of the timer 12 also generates at least one signal. It should be appreciated that the timer 12 may alternatively be activated by insertion of the surgical prep solution (e.g., a frangible ampoule) into the reservoir 20 via a triggering mechanism (not shown).

Once the absorbent pad 16 is saturated with the surgical prep solution, the surgical prep solution can be applied to a bodily surface (Step 58). The bodily surface onto which the surgical prep solution is applied will depend upon the type of medical procedure to be performed. For a Caesarian section, for example, the absorbent pad 16 can be contacted with the skin of a patient's abdomen. During application of the surgical prep solution, the timer 12 continues to generate the signal. After applying the surgical prep solution to the bodily surface (e.g., the surgical site), use of the applicator 10 is discontinued.

After discontinuing use of the applicator 10, the user can wait for a period of time until the signal is no longer perceptible (Step 60). For example, the timer 12 can continue to generate an audible and/or visible signal for about 3-5 minutes after discontinuing use of the applicator 10. Alternatively, the timer 12 can generate a second signal after discontinuing use of the applicator 10. The second signal can be the same as or different from the first signal, and can persist for a period of time (e.g., about 3-5 minutes) until the surgical prep solution has evaporated or dried. The period of time following application of the surgical prep solution (and before which the signal is generated) corresponds to the time needed for the surgical prep solution to evaporate or dry. Thus, once the signal is no longer discernable by the healthcare practitioner(s), the healthcare practitioner(s) (e.g., surgical team) will know that the surgical prep solution is evaporated or dried.

After the surgical prep solution has evaporated or dried, the medical procedure can be commenced without fear of igniting unevaporated surgical prep solution during the medical procedure.

Figure 4:
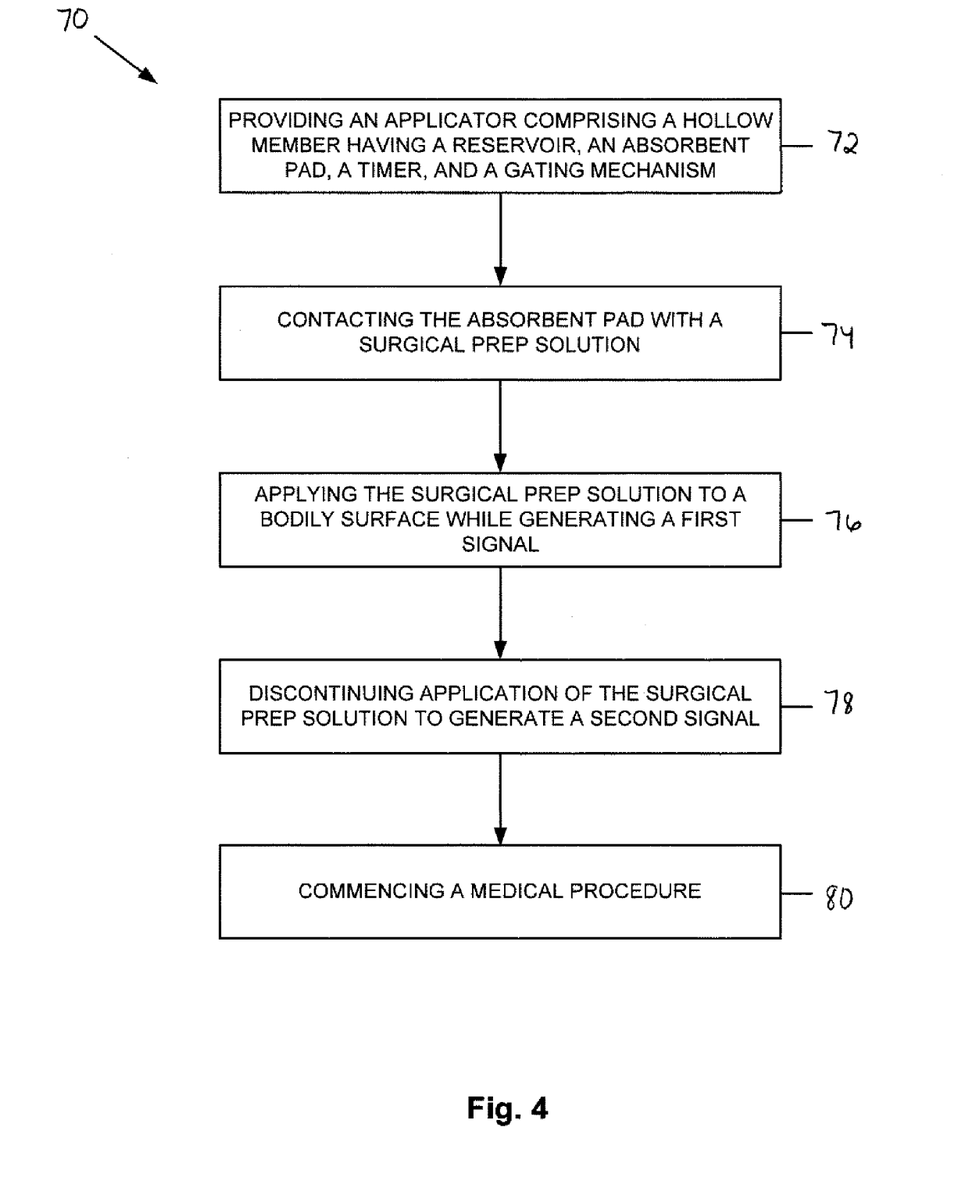
FIG. 4 is a process flow diagram illustrating a method for applying a surgical prep solution onto a bodily surface in accordance with yet another aspect of the present invention.

Another aspect of the present invention is illustrated in FIG. 4 and includes a method 70 for applying a surgical prep solution to a bodily surface. The method 70 combines the passive and active mechanisms of the methods 38 and 52, respectively, as described above. As shown in FIG. 4, the method 70 includes providing an applicator 10 at Step 72. The applicator 10 can be constructed in an identical or similar fashion as the applicator shown in FIGS. 1A-B and described in the method 52 (FIG. 3) above.

At Step 74 (FIG. 4), the surgical prep solution is released from the reservoir 20 (e.g., by compressing or breaking a container of the surgical prep solution) and contacts the absorbent pad 16. At or about the same time, the timer 12 is activated and, depending upon the preference of the user, the type of medical procedure, the type of surgical prep solution, etc., initiates a count-down or count-up sequence. Activation of the timer 12 also generates a first signal. It should be appreciated that the timer 12 may alternatively be activated by insertion of the surgical prep solution (e.g., a frangible ampoule) into the reservoir 20 via a triggering mechanism (not shown).

Once the absorbent pad 16 is saturated with the surgical prep solution, the surgical prep solution can be applied to a bodily surface (Step 76). The bodily surface onto which the surgical prep solution is applied will depend upon the type of medical procedure to be performed. For a Caesarian section, for example, the absorbent pad 16 can be contacted with the skin of a patient's abdomen. During application of the surgical prep solution, the timer 12 continues to generate the first signal. After applying the surgical prep solution to the bodily surface (e.g., the surgical site), use of the applicator 10 is discontinued.

After discontinuing use of the applicator 10, the timer 12 can discontinue the first signal and generate a second signal (Step 78). The second signal can be the same as or different from the first signal, and can persist for a period of time (e.g., about 3-5 minutes) until the surgical prep solution has evaporated or dried. Alternatively, the second signal may persist only briefly so that the user will know that the surgical prep solution is no longer being applied. The user can then wait for a period of time (e.g., 3-5 minutes) until the surgical prep solution has evaporated or dried. After the surgical prep solution has evaporated or dried, the medical procedure can be commenced (Step 80) without fear of igniting unevaporated surgical prep solution during the medical procedure.

From the above description of the invention, those skilled in the art will perceive improvements, changes and modifications. Such improvements, changes, and modifications are within the skill of the art and are intended to be covered by the appended claims.

The following is claimed:

1. An applicator for dispensing a surgical prep solution onto a bodily surface, said applicator comprising:
   a hollow member including a reservoir;
   an absorbent pad attached to a portion of said hollow member, said absorbent pad being in fluid communication with said reservoir;
   a timer operably connected to said hollow member; and
   a gating mechanism for coordinating application of the surgical prep solution with activation of said timer, said gating mechanism being in electrical communication with said timer;
   wherein release of the surgical prep solution from said reservoir is prevented until said timer is activated.

2. The applicator of claim 1, wherein said timer is physically integrated with a portion of said hollow member.

3. The applicator of claim 1, wherein said timer is capable of generating at least one signal.

4. The applicator of claim 1, wherein said at least one signal comprises an audible signal or a visible signal.

5. The applicator of claim 4, wherein said timer generates an audible and/or visible signal upon application of the surgical prep solution onto the bodily surface for a period of time sufficient to allow evaporation of the surgical prep solution from the bodily surface.

6. The applicator of claim 4, wherein said timer generates an audible and/or visible signal after a period of time sufficient to allow evaporation of the surgical prep solution from the bodily surface.

7. The applicator of claim 1, further including a communication protocol configured to communicate with an electronic medical record (EMR) of a patient undergoing a medical procedure in which said apparatus is being used, wherein communication between said communication protocol and said EMR documents safety compliance during the medical procedure.

8. A method for applying a surgical prep solution to a bodily surface, said method comprising the steps of:
   providing an applicator comprising a hollow member including a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer;
   dispensing the surgical prep solution onto the bodily surface while the timer generates at least one signal; and
   commencing a medical procedure once the at least one signal is no longer perceptible.

9. The method of claim 8, wherein the at least one signal comprises an audible signal or a visible signal.

10. The method of claim 8, wherein release of the surgical prep solution from the reservoir is prevented until the timer is activated.

11. The method of claim 8, wherein said step of providing an applicator further comprises providing a communication protocol configured to communicate with an EMR of a patient undergoing the medical procedure, wherein communication between the communication protocol and the EMR documents safety compliance during the medical procedure.

12. A method for applying a surgical prep solution to a bodily surface, said method comprising the steps of:
   providing an applicator comprising a hollow member including a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer;
   dispensing the surgical prep solution onto the bodily surface; and
   waiting to commence a medical procedure until the timer generates at least one signal.

13. The method of claim 12, wherein prior to said dispensing step the surgical prep solution is caused to contact the absorbent pad and activate the timer but without generating the at least one signal.

14. The method of claim 12, wherein the at least one signal comprises an audible signal or a visible signal.

15. The method of claim 12, wherein release of the surgical prep solution from the reservoir is prevented until the timer is activated.

16. The method of claim 12, wherein said step of providing an applicator further comprises providing a communication protocol configured to communicate with an EMR of a patient undergoing the medical procedure, wherein communication between the communication protocol and the EMR documents safety compliance during the medical procedure.

17. A method for applying a surgical prep solution to a bodily surface, said method comprising the steps of:
   providing an applicator comprising a hollow member including a reservoir, an absorbent pad that is attached to a portion of the hollow member and in communication with the reservoir, a timer operably connected to the hollow member, and a gating mechanism in electrical communication with the timer and for coordinating application of the surgical prep solution with activation of the timer;

dispensing the surgical prep solution onto the bodily surface while the timer generates a first signal;
discontinuing application of the surgical prep solution when the timer generates a second signal; and
commencing a medical procedure.

18. The method of claim 17, wherein said step of providing an applicator further comprises providing a communication protocol configured to communicate with an EMR of a patient undergoing the medical procedure, wherein communication between the communication protocol and the EMR documents safety compliance during the medical procedure.

* * * * *